United States Patent [19]

Falling et al.

[11] Patent Number: 4,962,210

[45] Date of Patent: Oct. 9, 1990

[54] PROCESS FOR THE PREPARATION OF HIGH-PURITY TETRAHYDROFURAN

[75] Inventors: Stephen N. Falling; Bruce L. Gustafson, both of Kingsport, Tenn.

[73] Assignee: Eastman Kodak Company, Rochester, N.Y.

[21] Appl. No.: 503,504

[22] Filed: Apr. 2, 1990

[51] Int. Cl.$^5$ .......................................... C07D 307/08
[52] U.S. Cl. .................................... 549/429; 549/507
[58] Field of Search ........................................ 549/429

[56] References Cited

U.S. PATENT DOCUMENTS 2,561,984  7/1954  Hillyer et al. .................. 549/512 X
3,021,342  2/1962  Manley ........................... 549/429 X
3,021,343  2/1962  Manley ........................... 549/429 X

OTHER PUBLICATIONS

Japanese 61-200,979–Derwent Abstract.

*Primary Examiner*—Richard L. Raymond
*Attorney, Agent, or Firm*—J. Frederick Thomsen; William P. Heath, Jr.

[57] ABSTRACT

Disclosed is a process for the preparation of high-purity tetrahydrofuran from a mixture of 2,5-dihydrofuran and 3,4-epoxy-1-butene and/or crotonaldehyde wherein the mixture is hydrogenated in the presence of a nickel or platinum catalyst to obtain a product consisting essentially of tetrahydrofuran and 1-butanol which are readily separable.

5 Claims, No Drawings

PROCESS FOR THE PREPARATION OF HIGH-PURITY TETRAHYDROFURAN

This invention pertains to a novel process for the preparation of high-purity tetrahydrofuran by the catalytic hydrogenation of dihydrofuran containing certain minor amounts of other compounds. More specifically, this invention pertains to the preparation of tetrahydrofuran and 1-butanol by the nickel-catalyzed hydrogenation of 2,5-dihydrofuran which contains as impurities small amounts of 3,4-epoxy-1-butene and/or crotonaldehyde (2-butenal).

Tetrahydrofuran and 1-butanol are useful as chemical intermediates and solvents. Tetrahydrofuran especially is a high-value industrial solvent and monomer. Most tetrahydrofuran is produced from acetylene and formaldehyde using Reppe chemistry with a minor amount being obtained furfural.

Monnier and Muehlbauer describe in U.S. Pat. No. 4,897,498 and U.S. patent application No. 07/292,589 processes for the preparation of 3,4-epoxy-1-butene by the selective epoxidation of 1,3-butadiene. Monnier and coworkers have further discovered gas phase processes for the isomerization of 3,4-epoxy-1-butene to 2,5-dihydrofuran wherein 3,4-epoxy-1-butene is contacted with a quaternary iodide salt of a Group VA element. Processes for the liquid phase rearrangement of 3,4-epoxy-1-butene to 2,5-dihydrofuran are described in U.S. Pat. Nos. 3,932,468 and 3,996,248.

The above described rearrangement processes give 2,5-dihydrofuran (bp 66° C.) containing 3,4-epoxy-1-butene (bp 66° C.), furan (bp 32° C.) and crotonaldehyde (bp 104° C.). Although furan and crotonaldehyde are separable from the 2,5-dihydrofuran by distillation, 3,4-epoxy-1-butene is not. U.S. Pat. No. 3,163,660 describes a purification process wherein 2,5-dihydrofuran is distilled from aqueous acid and maleic anhydride. The aqueous acid converts one or more impurities to readily-separable compounds and the maleic anhydride removes furan by a Diels-Alder reaction. However, the distillate obtained is a 2,5-dihydrofuran/water azeotrope (bp 64°–65° C.) composed of 93.9 weight percent 2,5-dihydrofuran and 6.1 weight percent water. Thus, further purification to remove the water is required.

In view of the state of the art described hereinabove, it is apparent that the most efficient means for obtaining essentially pure tetrahydrofuran, e.g., 98+ percent pure, is the catalytic hydrogenation of crude 2,5-dihydrofuran containing the above-mentioned impurities to a product mixture consisting essentially of tetrahydrofuran and another single compound which is readily separable from the high-value tetrahydrofuran. The catalytic hydrogenation of 3,4-epoxy-1-butene using palladium and Raney nickel catalysts is described in U.S. Pat. No. 2,561,984. According to this patent, the hydrogenation of 1,2-epoxybutane in ethanol solvent produces a substantial amount of secondary butyl alcohol (2-butanol) which is an undesirable product since it is not readily separable from tetrahydrofuran.

We have found that the hydrogenation of 3,4-epoxy-1-butene in tetrahydrofuran in the presence of Raney nickel at low pressures and temperatures results in the formation of large amounts of 1,2-epoxybutane. In view of the results reported in U.S. Pat. No. 2,561,984 (referred to above), one would expect the process of our invention to produce significant amounts of 2-butanol. However, the hydrogenation in the presence of tetrahydrofuran in accordance with our invention gives 1-butanol as the primary alkanol co-product.

U.S Pat. Nos. 3,021,342 and 3,021,343 describe the hydrogenation of furan, 2-methylfuran and dihydrofuran over supported nickel catalysts. These patents disclose that the temperature should be maintained below 120° C. to obtain high yields of tetrahydrofuran.

We have discovered that mixtures of 2,5-dihydrofuran and 3,4-epoxy-1-butene and/or crotonaldehyde may be hydrogenated to a mixture of tetrahydrofuran and 1-butanol using a nickel or platinum catalyst. The process of this invention thus provides a means for the preparation of highly pure tetrahydrofuran from a mixture of 2,5-dihydrofuran and 3,4-epoxy-1-butene and/or crotonaldehyde by the steps of (1) hydrogenating the mixture in the presence of a nickel or platinum catalyst to obtain a mixture consisting essentially of tetrahydrofuran and 1-butanol and (2) separating the tetrahydrofuran (bp 67° C.) from the 1-butanol (bp 117° C.).

The crude 2,5-dihydrofuran used in accordance with our process may contain up to 30 weight percent of 3,4-epoxy-1-butene and/or crotonaldehyde, typically about 3 to 8 weight percent 3,4-epoxy-1-butene and about 3 to 10 weight percent crotonaldehyde. The crude 2,5-dihydrofuran also may contain up to about 5 weight percent furan which is hydrogenated to tetrahydrofuran.

The hydrogenation conditions of temperature and pressure can be varied widely. Thus, the process may be conducted at a temperature in the range of about 25° to 200° C. and a total pressure of about 1 to 345 bar gauge. Preferred hydrogenation conditions are a temperature in the range of about 50° to 150° C. and a total pressure in the range of about 1 to 55 bar.

Although the process may be carried out in the absence of a solvent, the use of an inert organic solvent or diluent normally is preferred to control the temperature since the reaction is exothermic and considerable heat is generated by the hydrogenation. Solvents which may be used include aliphatic and aromatic hydrocarbons such as heptane, toluene, specific or mixed xylenes and the like and alkanols such as ethanol and butanol. The use of tetrahydrofuran as the solvent/diluent is especially preferred since the recovery and recycle of a material extraneous to the process is avoided. The weight ratio of crude 2,5-dihydrofuran, i.e., a mixture of 2,5-dihydrofuran and 3,4-epoxy-1-butene, crotonaldehyde and/or furan, to solvent may range from 1:99 to 50:50.

The process may be carried out in a batch, semicontinuous or continuous mode of operation. For example, batch operation may comprise agitating a slurry of a catalyst, e.g., Raney nickel, platinum oxide or a supported nickel or platinum catalyst, in crude 2,5-dihydrofuran and, optionally, a solvent in a pressure vessel for a time sufficient to convert essentially all of the components of the crude 2,5-dihydrofuran to tetrahydrofuran and 1-butanol. The catalyst can be separated from the hydrogenated mixture by filtration and the components (tetrahydrofuran and 1-butanol) of the filtrate separated by distillation.

The preferred mode of operations uses a fixed bed of a supported nickel or platinum catalyst wherein crude 2,5-dihydrofuran is hydrogenated in the gas or, especially, liquid phase, optionally in the presence of an inert diluent. Liquid phase operation typically involves feeding a solution of the crude 2,5-dihydrofuran in an inert solvent-diluent to the top of a columnar, pressure reactor containing one or more fixed beds of the supported catalyst. The reactant solution flows (trickles) over the catalyst bed in the presence of hydrogen at elevated temperature and pressure and the hydrogenated product exits the bottom of the reactor and is separated into its components by distillation. The feed rates employed in liquid phase operation may be in the range of about 0.01 to 100 liquid hour space velocities (LHSV, unit volume of feed per unit volume of catalyst). Under most conditions, the LHSV will be in the range of about 0.1 to 10.

The catalyst may be selected from Raney nickel, various platinum compounds such as platinum oxide and various supported nickel and platinum catalysts, depending on the mode of operation. The supported catalyst comprise nickel or platinum deposited on a catalyst support material such as silica, alumina, carbon, titanium dioxide, molecular sieves, zeolites, kieselguhr, etc. Normally, the supported nickel catalysts are comprised of about 1 to 90 weight percent nickel, calculated as [Ni], based on the total weight of the catalyst. Preferred nickel supported catalysts comprise about 1 to 70 weight percent on silica/alumina. The platinum content of the supported platinum catalysts may be in the range of about 0.1 to 20 weight percent platinum. The preferred supported platinum catalyst are comprised of about 0.5 to 5.0 weight percent platinum on alumina. The process preferably is carried out in the presence of one of the described nickel catalysts.

Our novel process is further illustrated by the following examples.

EXAMPLE 1

To a nitrogen-purged, glass autoclave liner was added a Teflon-coated magnetic stirring bar and waterwet Raney nickel (0.50 g) which was rinsed twice with water and then three times with a small amount of tetrahydrofuran. The following materials were added to the liner:

28.00 g (1.0830 mol) tetrahydrofuran
35.02 g (0.4996 mol) 2,5-dihydrofuran
2.05 g (0.0292 mol) 3,4-epoxy-1-butene
2.01 g (0.0287 mol) crotonaldehyde The resulting mixture was hydrogenated in a magnetically-stirred autoclave at 115°–120° C. and 34.5 bar (gauge) total pressure for 4 hours. Gas chromatography analysis (GCA) of the crude product showed 0.11% low boilers, 0.39% of combined 3,4-epoxy-1-butene/1,2-epoxybutane, 95.15% tetrahydrofuran and 4.25% 1-butanol.

The crude product was separated from the catalyst and fractionally distilled and product was collected over a temperature of 55°–67° C. The product (109.46 g, 96.1% of theory) consisted of 0.06% low boilers, 0.32% combined 3,4-epoxy-1-butene/butyraldehyde, 0.08% 1-butanol and 99.54% tetrahydrofuran by GCA.

EXAMPLE 2

A fixed catalyst bed apparatus was constructed using a 1 inch by 24 inch 316 stainless steel tube which contained a 4.5 inch (30.4 g, 39 cc) bed of 50% nickel on alumina (Harshaw Ni-3276, 0.125 inch extrudates) supported by a layer of 0.125 inch 316 stainless steel packing. A layer of packing also was placed above the catalyst bed to ensure adequate liquid distribution and preheating of the feed prior to contact with the catalyst. A thermocouple was positioned in the middle of the catalyst bed.

Pressure was controlled with a Circle Dome loaded back pressure regulator and gas flow rated were controlled using Brooks mass flow controllers capable of operation of up to 310 bar. Prior to the start of the feed materials, the catalyst bed was heated to 260° C. with a nitrogen flow to remove carbon dioxide from the passivated catalyst. After removal of carbon dioxide the gas was switched to hydrogen and the reactor was cooled to the desired temperature. The product mixture was collected in a flask fitted with a condenser held at −20° C. The gas exiting this trapping system was analyzed using an on-line gas chromatograph calibrated for $C_1$–$C_6$ hydrocarbons. The liquid collected was analyzed by GCA.

A mixture consisting of 5 weight percent, 3,4-epoxy-1-butene, 5 weight percent crotonaldehyde, 20 weight percent 2,5-dihydrofuran and 70 weight percent tetrahydrofuran was fed to above-described reactor at 100° C. and 5.5 bar (gauge) at a feed rate of 142 g per hour while feeding hydrogen at the rate of 800 standard cc per minute. The reactor temperature rose to 148° C. during the experiment. The product obtained contained (by GCA) 89% tetrahydrofuran, 11% 1-butanol along with a trace of butyraldehyde.

The invention has been described in detail with particular reference to preferred embodiments thereof, but it will be understood that variations and modifications can be effected within the spirit and scope of the invention.

We claim:

1. Process for the preparation of high-purity tetrahydrofuran from a mixture of 2,5-dihydrofuran and 3,4-epoxy-1-butene and/or crotonaldehyde which comprises the steps of (1) hydrogenating the mixture in the presence of a nickel or platinum catalyst to obtain a mixture consisting essentially of tetrahydrofuran and 1-butanol and (2) separating the tetrahydrofuran from the 1-butanol.

2. Process according to claim 1 wherein the mixture is composed of a mixture of 2,5-dihydrofuran, about 3 to 8 weight percent 3,4-epoxy-1-butene and about 3 to 10 weight percent crotonaldehyde.

3. Process for the preparation of high-purity tetrahydrofuran from a mixture comprised of 2,5-dihydrofuran, about 3 to 8 weight percent 3,4-epoxy-1-butene and about 3 to 10 weight percent crotonaldehyde which comprises the steps of (1) hydrogenating the mixture in the presence of a nickel catalyst at about 50° to 150° C and 1 to 55 bar to obtain a mixture consisting essentially of tetrahydrofuran and 1-butanol and (2) separating the tetrahydrofuran from the 1-butanol.

4. Process according to claim 3 wherein the mixture hydrogenated contains tetrahydrofuran.

5. Process according to claim 3 wherein the mixture hydrogenated contains tetrahydrofuran and the nickel catalyst comprises about 1 to 70 weight percent nickel on silica/alumina.

* * * * *